US009535173B2

(12) United States Patent
Liu et al.

(10) Patent No.: US 9,535,173 B2
(45) Date of Patent: *Jan. 3, 2017

(54) ORGANIC X-RAY DETECTOR AND X-RAY SYSTEMS

(71) Applicant: General Electric Company, Schenectady, NY (US)

(72) Inventors: Jie Jerry Liu, Niskayuna, NY (US); Kwang Hyup An, Rexford, NY (US); Aaron Judy Couture, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 119 days.

This patent is subject to a terminal disclaimer.

(21) Appl. No.: 14/483,198

(22) Filed: Sep. 11, 2014

(65) Prior Publication Data

US 2016/0077221 A1    Mar. 17, 2016

(51) Int. Cl.
*G01T 1/20*     (2006.01)
*G01T 1/24*     (2006.01)
(Continued)

(52) U.S. Cl.
CPC . *G01T 1/24* (2013.01); *A61B 6/42* (2013.01); *A61B 6/4208* (2013.01);
(Continued)

(58) Field of Classification Search
CPC ... A61B 6/4208; A61B 6/4233; A61B 6/4283; G01T 1/2018; G01T 1/24; H01L 51/0032; H01L 51/0034
(Continued)

(56) References Cited

U.S. PATENT DOCUMENTS 5,179,284 A      1/1993  Kingsley et al.
6,214,210 B1 *   4/2001  White ................... B23K 31/12
                                                    204/414
(Continued)

FOREIGN PATENT DOCUMENTS

DE    102006015043 A1    10/2007
DE    102011084276 A1     4/2013
(Continued)

OTHER PUBLICATIONS

PCT Search Report and Written Opinion issued in connection with corresponding Application No. PCT/US2015/043120 on Oct. 29, 2015.

(Continued)

*Primary Examiner* — Allen C. Ho
(74) *Attorney, Agent, or Firm* — Melissa K. Dobson

(57) ABSTRACT

An organic x-ray detector is presented. The organic x-ray detector includes a layered structure. The layered structure includes a thin-film transistor (TFT) array disposed on a substrate, an organic photodiode disposed on the TFT array, and a scintillator layer disposed on the organic photodiode. The organic x-ray detector includes an encapsulation cover at least partially encapsulating the layered structure. The organic x-ray detector further includes at least one of a moisture getter layer and an oxygen getter layer disposed proximate to the organic photodiode, and in the path of an x-ray radiation incident on the layered structure. X-ray system including the organic x-ray detector is also presented.

20 Claims, 10 Drawing Sheets

(51) Int. Cl.
  A61B 6/00 (2006.01)
  G01N 23/04 (2006.01)
  H01L 27/30 (2006.01)
  G01T 1/202 (2006.01)
  *H01L 51/00* (2006.01)
  *H01L 51/42* (2006.01)
  *H01L 51/52* (2006.01)

(52) U.S. Cl.
  CPC .......... *A61B 6/4233* (2013.01); *A61B 6/4283* (2013.01); *G01N 23/04* (2013.01); *G01T 1/20* (2013.01); *G01T 1/202* (2013.01); *G01T 1/2018* (2013.01); *H01L 27/308* (2013.01); *H01L 51/0036* (2013.01); *H01L 51/0039* (2013.01); *H01L 51/0043* (2013.01); *H01L 51/4253* (2013.01); *H01L 51/5259* (2013.01)

(58) Field of Classification Search
  USPC .............................. 378/19, 98.8; 250/370.09
  See application file for complete search history.

(56) References Cited

U.S. PATENT DOCUMENTS

| | | | |
|---|---|---|---|
| 6,455,620 B1 | 9/2002 | Cyr et al. | |
| 6,642,524 B2 | 11/2003 | Vafi et al. | |
| 6,680,094 B2 | 1/2004 | Kikuchi et al. | |
| 6,982,424 B2 | 1/2006 | Vafi et al. | |
| 7,053,381 B2 | 5/2006 | Shaw et al. | |
| 7,696,722 B2 | 4/2010 | Utschig et al. | |
| 7,847,258 B2* | 12/2010 | Yaegashi | G01T 1/2018 250/370.08 |
| 8,053,984 B2 | 11/2011 | Lee et al. | |
| 8,206,841 B2 | 6/2012 | Fujita et al. | |
| 8,236,727 B2 | 8/2012 | Ohta et al. | |
| 8,415,628 B1 | 4/2013 | Shaw et al. | |
| 8,431,721 B2 | 4/2013 | Deshpande et al. | |
| 8,431,902 B2* | 4/2013 | Nakatsugawa | A61B 6/4208 250/361 R |
| 8,497,481 B2 | 7/2013 | Shinba et al. | |
| 8,550,709 B2* | 10/2013 | Nishino | A61B 6/04 378/145 |
| 8,579,506 B2 | 11/2013 | Morton | |
| 8,581,254 B2 | 11/2013 | Couture et al. | |
| 8,618,491 B2* | 12/2013 | Shimizukawa | A61B 6/4233 250/370.09 |
| 8,729,484 B2* | 5/2014 | Nishino | G01T 1/2018 250/370.09 |
| 8,735,829 B2* | 5/2014 | Kuwabara | A61B 6/4233 250/362 |
| 8,742,354 B2* | 6/2014 | Shimizukawa | G01T 1/16 250/354.1 |
| 8,748,834 B2* | 6/2014 | Enomoto | A61B 6/4233 250/370.08 |
| 8,791,420 B2* | 7/2014 | Nariyuki | G01T 1/20 250/366 |
| 8,796,633 B2* | 8/2014 | Nakatsugawa | G01T 1/2002 250/370.11 |
| 8,798,235 B2* | 8/2014 | Ohta | G01N 23/04 250/370.09 |
| 8,829,455 B2* | 9/2014 | Nakatsugawa | A61B 6/4233 250/370.09 |
| 8,841,628 B2* | 9/2014 | Kitano | H01L 27/14663 250/393 |
| 8,859,985 B2* | 10/2014 | Yasui | G01N 23/223 250/336.1 |
| 8,981,304 B2* | 3/2015 | Okada | G01T 1/2018 250/354.1 |
| 8,981,309 B2* | 3/2015 | Noguchi | G03B 42/04 250/370.01 |
| 9,044,191 B2* | 6/2015 | Nishino | A61B 6/4405 |
| 9,050,051 B2* | 6/2015 | Nakatsugawa | A61B 6/4233 |
| 9,063,239 B2* | 6/2015 | Oda | G01T 1/24 |
| 9,140,809 B2* | 9/2015 | Nakahashi | G01T 1/2018 |
| 9,158,004 B2* | 10/2015 | Oda | G01T 1/17 |
| 9,182,504 B2* | 11/2015 | Nishino | G01T 1/2018 |
| 9,194,964 B2* | 11/2015 | Ito | H04N 5/32 |
| 9,257,480 B2* | 2/2016 | Zhao | H01L 27/14812 |
| 9,258,464 B2* | 2/2016 | Ohta | H04N 5/321 |
| 9,268,041 B2* | 2/2016 | Ohta | G01T 1/2018 |
| 9,282,943 B2* | 3/2016 | Oda | A61B 6/5258 |
| 9,335,422 B2* | 5/2016 | Oda | G01T 1/17 |
| 2006/0163534 A1 | 7/2006 | Sugimoto et al. | |
| 2007/0184300 A1 | 8/2007 | Yokose et al. | |
| 2008/0142721 A1 | 6/2008 | Spahn | |
| 2009/0084961 A1 | 4/2009 | Tonotani et al. | |
| 2010/0207112 A1 | 8/2010 | Furst et al. | |
| 2012/0241628 A1 | 9/2012 | Hesser et al. | |
| 2012/0318348 A1 | 12/2012 | Frazier et al. | |
| 2013/0199603 A1 | 8/2013 | Snaith et al. | |
| 2014/0246665 A1 | 9/2014 | Lang et al. | |
| 2015/0144889 A1* | 5/2015 | An | G01T 1/2018 257/40 |
| 2015/0171134 A1* | 6/2015 | Couture | H01L 27/14632 250/366 |
| 2016/0027847 A1* | 1/2016 | Liu | G01N 23/04 378/62 |
| 2016/0064680 A1* | 3/2016 | An | H01L 51/448 378/62 |
| 2016/0111473 A1* | 4/2016 | Liu | G01T 1/2018 378/51 |

FOREIGN PATENT DOCUMENTS

| EP | 1253171 B1 | 6/2009 |
|---|---|---|
| EP | 2251713 A1 | 11/2010 |

OTHER PUBLICATIONS

Li et al., "Development of a simple device for a moisture-proof X-ray diffraction analysis", Journal of Powder Diffraction, Cambridge University Press ,Sep. 1997, vol. 12, Issue 03, pp. 145-150.
Morlat et al.,"Phototransformation of water-soluble polymers. I: photo- and thermooxidation of poly(ethylene oxide) in solid stater",Polymer, ScienceDirect, Jun. 2001, vol. 42, Issue 14, pp. 6071-6079.
Lee et al., "The effect of monomer structure on oxygen inhibition of (meth)acrylates photopolymerization", Polymer, ScienceDirect, Aug. 19, 2004,vol. 45, Issue 18, pp. 6155-6162.
Vacca et al., "Dispensable Getter Materials for lifetime insurance in Organic Electronics", SAES Getters, Organic Electronics : principles, devices and applications, Politecnico di Milano, Nov. 18, 2011, 36 Pages.
Parthasarathy et al., "Organic X-Ray Detector", Pending U.S. Appl. No. 13/955,355, filed Jul. 31, 2013, 22 Pages.
An et al., "Organic X-Ray Detector With Barrier Layer", Pending U.S. Appl. No. 14/087,774, filed Nov. 22, 2013, 16 Pages.

* cited by examiner

ORGANIC X-RAY DETECTOR AND X-RAY SYSTEMS

BACKGROUND

Embodiments of the invention generally relate to organic x-ray detectors. More particularly, embodiments of the invention relate to organic x-ray detectors including oxygen and moisture getter layers.

Digital x-ray detectors fabricated with continuous photodiodes have potential applications for low cost digital radiography as well as for rugged, light-weight and portable detectors. Digital x-ray detectors with continuous photodiodes have an increased fill factor and potentially higher quantum efficiency. The continuous photodiode generally includes organic photodiodes (OPDs). A scintillator which converts x-ray to visible light is generally disposed on top of the OPDs.

Typical organic x-ray detectors are subject to performance degradation upon exposure to oxygen and/or moisture. Possible degradation mechanisms include one or both of oxidation of electrode materials and oxidation of organic materials (e.g., OPD materials). During the post OPD deposition process, such as, scintillator deposition, encapsulation, laser repair, or operation, OPD has a high chance of exposure to air. Most organic based photodiodes are sensitive to oxygen and/or moisture, and hence need to be protected from the oxygen-containing air. A hermetic seal is thus desirable to achieve a reliable OPD and organic x-ray detector. Typical x-ray detectors include a top cover along with edge seals. However, edge sealants are generally more permeable for moisture and oxygen than the top cover, and edge ingress of moisture/oxygen may be a limiting factor for long-term stability.

Therefore, there is a need for x-ray detector configurations with improved oxygen and moisture getter layers.

BRIEF DESCRIPTION

In one aspect, the invention relates to an organic x-ray detector. The organic x-ray detector includes a layered structure. The layered structure includes a thin-film transistor (TFT) array disposed on a substrate, an organic photodiode disposed on the TFT array, and a scintillator layer disposed on the organic photodiode. The organic x-ray detector includes an encapsulation cover at least partially encapsulating the layered structure. The organic x-ray detector further includes at least one of a moisture getter layer and an oxygen getter layer disposed proximate to the organic photodiode, and in the path of an x-ray radiation incident on the layered structure.

In another aspect, the invention relates to an organic x-ray detector including a layered structure. The layered structure includes a thin-film transistor (TFT) array disposed on a substrate, an organic photodiode disposed on the TFT array, and a scintillator layer disposed on the organic photodiode. The organic x-ray detector includes an encapsulation cover at least partially encapsulating the layered structure. The organic x-ray detector further includes an oxygen getter layer disposed between the organic photodiode and the scintillator layer in the layered structure; and a moisture getter layer disposed in contact with at least a portion of the encapsulation cover.

In yet another aspect, the invention relates to an x-ray system. The x-ray system includes an x-ray source; an organic x-ray detector; and a processor operable to process data from the organic x-ray detector. The organic x-ray detector includes a layered structure. The layered structure includes a thin-film transistor (TFT) array disposed on a substrate, an organic photodiode disposed on the TFT array, and a scintillator layer disposed on the organic photodiode. The organic x-ray detector includes an encapsulation cover at least partially encapsulating the layered structure. The organic x-ray detector further includes at least one of a moisture getter layer and an oxygen getter layer disposed proximate to the organic photodiode, and in the path of an x-ray radiation incident on the layered structure.

These and other features, embodiments, and advantages of the present invention may be understood more readily by reference to the following detailed description.

DRAWINGS

These and other features, aspects, and advantages of the present invention will become better understood when the following detailed description is read with reference to the accompanying drawings, wherein.

DETAILED DESCRIPTION

Figure 1:
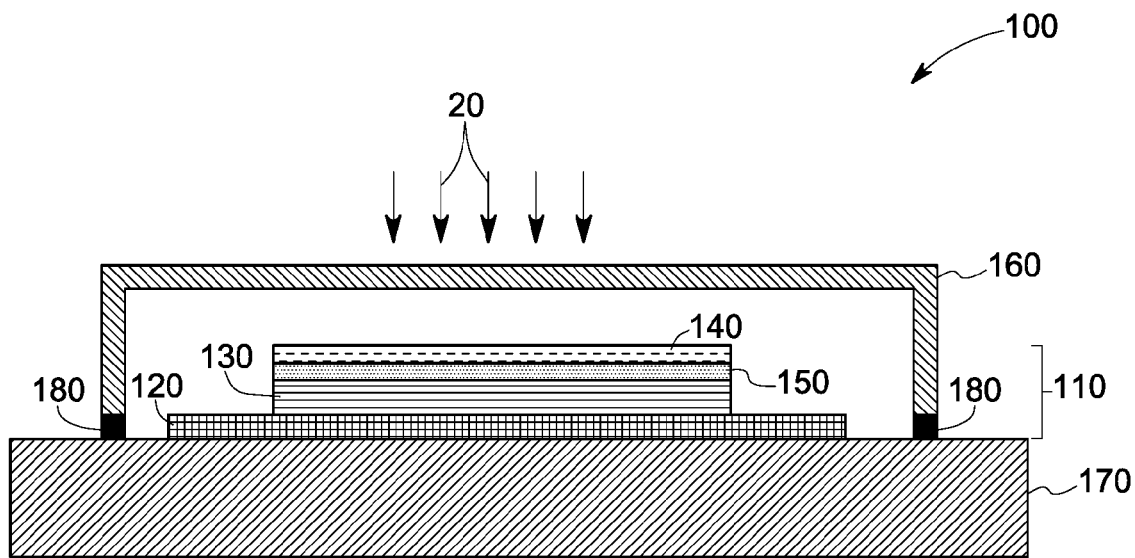
FIG. 1 is a schematic of an organic x-ray detector, according to one embodiment of the invention.

In the following specification and the claims, which follow, reference will be made to a number of terms, which shall be defined to have the following meanings. The singular forms "a", "an" and "the" include plural referents unless the context clearly dictates otherwise. "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", and "substantially" is not to be limited to the precise value specified. In some instances, the approximating language may correspond to the precision of an instrument for measuring the value. Similarly, "free" may be used in combination with a term, and may include an insubstantial number, or trace amounts, while still being considered free of the modified term. Here and throughout the specification and claims, range limitations may be combined and/or interchanged, such ranges are identified and include all the sub-ranges contained therein unless context or language indicates otherwise.

As used herein, the term "layer" refers to a material disposed on at least a portion of an underlying surface in a continuous or discontinuous manner. Further, the term "layer" does not necessarily mean a uniform thickness of the disposed material, and the disposed material may have a uniform or a variable thickness. As used herein, the term "disposed on" refers to layers disposed directly in contact with each other or indirectly by having intervening layers there between, unless otherwise specifically indicated. The term "adjacent" as used herein means that the two layers are disposed contiguously and are in direct contact with each other.

In the present disclosure, when a layer is being described as "on" another layer or substrate, it is to be understood that the layers can either be directly contacting each other or have one (or more) layer or feature between the layers. Further, the term "on" describes the relative position of the layers to each other and does not necessarily mean "on top of" since the relative position above or below depends upon the orientation of the device to the viewer. Moreover, the use of "top," "bottom," "above," "below," and variations of these terms is made for convenience, and does not require any particular orientation of the components unless otherwise stated.

Electro-optical devices, such as, but not limited to, organic x-ray detectors include an electronically or optically active portion—e.g., scintillators and photodiodes that are frequently disposed on a substrate. In order to protect the active portion and the substrate from degradation due to exposure to moisture, oxygen, or corrosive chemical attack, the electro-optical devices are normally encased in a seal. Typical x-ray detectors include a top cover along with edge seals. However, edge sealants are generally more permeable for moisture and oxygen than the top cover, and edge ingress of moisture/oxygen may be a limiting factor for long-term stability.

One aspect of the invention is to provide an electro-optical device, such as, but not limited to, organic x-ray detectors. A schematic representation of such an organic x-ray detector (XRD) is shown in FIGS. 1-15. As shown in FIGS. 1-15, an organic x-ray detector 100 includes a layered structure 110. The layered structure 110 includes a thin-film transistor (TFT) array 120 disposed on a substrate 170, an organic photodiode 130 disposed on the TFT array 120, and a scintillator layer 140 disposed on the organic photodiode 130. The organic x-ray detector 100 further includes an encapsulation cover 160 at least partially encapsulating the layered structure 110. The organic x-ray detector 100 further includes at least one of a moisture getter layer and an oxygen getter layer disposed proximate to the organic photodiode 130, and in the path of an x-ray radiation 20 incident on the layered structure 110.

As illustrated in FIGS. 1-15, the scintillator layer 140 is excited by impinging x-ray radiation 20 and produces visible light. Scintillator layer 140 may be composed of a phosphor material that is capable of converting x-rays to visible light. The wavelength region of light emitted by scintillator layer 140 may range from about 360 nm to about 830 nm. Suitable materials for the scintillator layer 140 include, but are not limited to, cesium iodide (CsI), CsI (Tl) (cesium iodide to which thallium has been added) and terbium-activated gadolinium oxysulfide (GOS). Such materials are commercially available in the form of a sheet or screen. Another scintillator that may be used is a PIB (particle in binder) scintillator, where scintillating particles may be incorporated in a binder matrix material and flattened on a substrate. The scintillator layer 140 may be a monolithic scintillator or pixelated scintillator array. The visible light generated by the scintillator layer 140 irradiates an organic photodiode 130 disposed on a TFT array 120.

Figure 16:
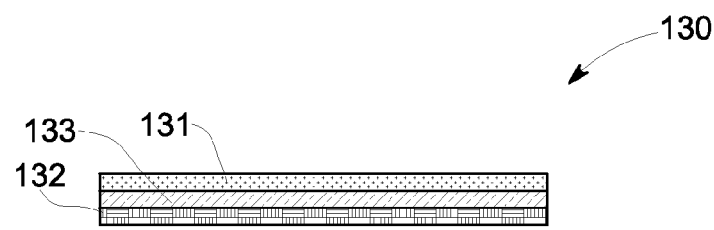
FIG. 16 is a schematic of an organic photodiode, according to one embodiment of the invention.

As shown in FIG. 16, the organic photodiode 130 includes a first electrode 131, a second electrode 132, and an absorber layer (sometimes also referred to as an "active layer") 133 interposed between the first electrode 131 and the second electrode 132. Depending on the application and variations in design, the absorber layer 133 may include a single organic layer or may include multiple organic layers. Further, the organic photodiode 130 may be directly disposed on the TFT array 120 or the design may include one or more layers disposed between the organic photodiode 130 and the TFT array 120.

The absorber layer 133 may be a bulk, hetero junction organic photodiode layer that absorbs light, separates charge and transports holes and electrons to the contact layers. In some embodiments, the absorber layer 133 may be patterned. Absorber layer 133 may include a blend of a donor material and an acceptor material; more than one donor material or acceptor material may be included in the blend. In some embodiments, the donor and acceptor may be incorporated in the same molecule. Further, the HOMO/LUMO levels of the donor and acceptor materials may be compatible with that of the first electrode 131 and second electrode 132 in order to allow efficient charge extraction without creating an energetic barrier.

Suitable donor materials include low bandgap polymers having LUMO ranging from about 1.9 eV to about 4.9 eV, particularly from 2.5 eV to 4.5 eV, more particularly from 3.0 eV to 4.5 eV; and HOMO ranging from about 2.9 eV to about 7 eV, particularly from 4.0 eV to 6 eV, more particularly from 4.5 eV to 6 eV. The low band gap polymers include conjugated polymers and copolymers composed of units derived from substituted or unsubstituted monoheterocyclic and polyheterocyclic monomers such as thiophene, fluorene, phenylenevinylene, carbazole, pyrrolopyrrole, and fused heteropolycyclic monomers containing the thiophene ring, including, but not limited to, thienothiophene, benzodithiophene, benzothiadiazole, pyrrolothiophene monomers, and substituted analogs thereof. In particular embodiments, the low band gap polymers comprise units derived from substituted or unsubstituted thienothiophene, benzodithiophene, benzothiadiazole, carbazole, isothianaphthene, pyrrole, benzo-bis(thiadiazole), thienopyrazine, fluorene, thiadiazoloquinoxaline, or combinations thereof. In the context of the low band gap polymers described herein, the term "units derived from" means that the units are each a residue comprising the monoheterocyclic and polyheterocyclic group, without regard to the substituents present before or during the polymerization; for example, "the low band gap polymers comprise units derived from thienothiophene" means that the low band gap polymers comprise divalent thienothiophenyl groups. Examples of suitable materials for use as low bandgap polymers in the organic x-ray detectors according to the present invention include copolymers derived from substituted or unsubstituted thienothiophene, benzodithiophene, benzothiadiazole or carbazole monomers, and combinations thereof, such as poly[[4,8-bis[(2-ethyl hexyl)oxy]benzo[1,2-b:4,5-b']dithiophene-2,6-diyl][3-fluoro-2-[(2-ethylhexyl)carbonyl]thieno[3,4-b]thiophenediyl (PTB7), 2,1,3-benzothiadiazole-4,7-diyl[4,4-bis(2-ethylhexyl)-4H-cyclopenta[2,1-b:3,4-b']dithiophene-2,6-diyl (PCPDTBT), poly[[9-(1-octylnonyl)-9H-carbazole-2,7-diyl]-2,5-thiophenediyl-2,1,3-benzothiadiazole-4,7-diyl-2,5-thiophenediyl] (PCDTBT), poly[(4,40-bis(2-ethylhexyl)dithieno[3,2-b:20,30-d]silole)-2,6-diyl-alt-(2,1,3-benzo-thiadiazole)-4,7-diyl] (PSBTBT), poly((4,8-bis (octyloxy)benzo(1,2-b:4,5-b')dithiophene-2,6-diyl)(2-((dodecyloxy)carbonyl)thieno(3,4-b)thiophenediyl)) (PTB1), poly((4,8-bis(octyloxy)benzo(1,2-b:4,5-b')dithiophene-2,6-diyl)(2-((ethylhexyloxy)carbonyl)thieno(3,4-b) thiophenediyl)) (PTB2), poly((4,8-bis(octyl)benzo(1,2-b:4, 5-b')dithiophene-2,6-diyl) (2-((ethylhexyloxy)carbonyl) thieno(3,4-b)thiophenediyl)) (PTB3), poly((4,8-bis-(ethylhexyloxybenzo(1,2-b:4,5-b')dithiophene-2,6-diyl)(2-((octyloxy)carbonyl)-3-fluoro)thieno(3,4-b)thiophenediyl)) (PTB4), poly((4,8-bis(ethylhexyloxybenzo(1,2-b:4,5-b')dithiophene-2,6-diyl)(2-((octyloxy)carbonyl)thieno(3,4-b) thiophenediyl)) (PTB5), poly((4,8-bis(octyloxy)benzo(1,2-b:4,5-b')dithiophene-2,6-diyl)(2-((butyloctyloxy)carbonyl) thieno(3,4-b)thiophenediyl)) (PTB6), poly[[5-(2-ethylhexyl)-5,6-dihydro-4,6-dioxo-4H-thieno[3,4-c] pyrrole-1,3-diyl][4,8-bis R2-ethylhexyl)oxy]benzo[1,2-b:4, 5-b']dithiophene-2,6-diyl]] (PBDTTPD), poly[1-(6-{4,8-bis R2-ethylhexyl)oxyl-6-methylbenzo[1,2-b:4,5-b']dithiophen-2-yl}-3-fluoro-4-methylthieno[3,4-b]thiophen-2-yl)-1-octanone] (PBDTTT-CF), and poly[2,1,3-benzothiadiazole-4,7-diyl-2,5-thiophenediyl(9,9-dioctyl-9H-9-silafluorene-2,7-diyl)-2,5-thiophenediyl] (PSiF-DBT). Other suitable materials are poly[5,7-bis(4-decanyl-2-thienyl)thieno[3,4-b]diathiazole-thiophene-2,5] (PDDTT), poly [2,3-bis(4-(2-ethylhexyloxy)phenyl)-5,7-di(thiophen-2-yl) thieno[3,4-b]pyrazine] (PDTTP), and polythieno[3,4-b] thiophene (PTT). In particular embodiments, suitable materials are copolymers derived from substituted or unsubstituted benzodithiophene monomers, such as the PTB1-7 series and PCPDTBT; or benzothiadiazole monomers, such as PCDTBT and PCPDTBT.

In particular embodiments, the donor material is a polymer with a low degree of crystallinity or is an amorphous polymer. Degree of crystallinity may be increased by substituting aromatic rings of the main polymer chain. Long chain alkyl groups containing six or more carbons or bulky polyhedral oligosilsesquioxane (POSS) may result in a polymer material with a lower degree of crystallinity than a polymer having no substituents on the aromatic ring, or having short chain substituents such as methyl groups. Degree of crystallinity may also be influenced by processing conditions and means, including, but not limited to, the solvents used to process the material and thermal annealing conditions. Degree of crystallinity is readily determined using analytical techniques such as calorimetry, differential scanning calorimetry, x-ray diffraction, infrared spectroscopy and polarized light microscopy.

Suitable materials for the acceptor material include fullerene derivatives such as [6,6]-phenyl-$C_{61}$-butyric acid methyl ester (PCBM), PCBM analogs such as $PC_{70}BM$, $PC_{71}BM$, $PC_{80}BM$, bis-adducts thereof, such as bis-$PC_{71}BM$, indene mono-adducts thereof, such as indene-$C_{60}$ monoadduct (ICMA) and indene bis-adducts thereof, such as indene-$C_{60}$ bisadduct (ICBA). Fluorene copolymers such as poly[(9,9-dioctylfluorenyl-2,7-diyl)-alt-(4,7-bis(3-hexylthiophen-5-yl)-2,1,3-benzothiadiazole)-2',2"-diyl] (F8TBT) may also be used, alone or with a fullerene derivative.

In one embodiment, the first electrode 131 functions as a cathode and the second electrode 132 as an anode. In another embodiment, the first electrode 131 functions as an anode and the second electrode 132 as a cathode. Suitable anode materials include, but are not limited to, metals such as Al, Ag, Au, and Pt, metal oxides such as indium tin oxide (ITO), indium zinc oxide (IZO), and zinc oxide (ZnO), and organic conductors such as p-doped conjugated polymers like PEDOT. Suitable cathode materials include transparent conductive oxides (TCO) and thin films of metals such as gold and silver. Examples of suitable TCO include ITO, IZO, aluminum zinc oxide (AZO), fluorinated tin oxide (FTO), tin oxide ($SnO_2$), titanium dioxide ($TiO_2$), ZnO, indium zinc oxide (In—Zn—O series), indium gallium oxide, gallium zinc oxide, indium silicon zinc oxide, indium gallium zinc oxide, or combinations thereof.

Referring again to FIGS. 1-15, the TFT array 120 may be a two dimensional array of passive or active pixels, which stores charge for read out by electronics, disposed on an active layer formed of amorphous silicon or an amorphous metal oxide, or organic semiconductors. In some embodiments, the TFT array 120 includes a silicon TFT array, an oxide TFT array, an organic TFT, or combinations thereof. Suitable amorphous metal oxides include zinc oxide, zinc tin oxide, indium oxides, indium zinc oxides (In—Zn—O series), indium gallium oxides, gallium zinc oxides, indium silicon zinc oxides, and indium gallium zinc oxides (IGZO). IGZO materials include $InGaO_3(ZnO)_m$, where m is ≤6 and $InGaZnO_4$. Suitable organic semiconductors include, but are not limited to, conjugated aromatic materials, such as rubrene, tetracene, pentacene, perylenediimides, tetracyanoquinodimethane and polymeric materials such as polythiophenes, polybenzodithiophenes, polyfluorene, polydiacetylene, poly(2,5-thiophenylene vinylene), poly(p-phenylene vinylene) and derivatives thereof.

The TFT array 120 is further disposed on a substrate 170. Suitable substrate 170 materials include glass, ceramics, plastics and metals. The substrate 170 may be present as a rigid sheet such as a thick glass, a thick plastic sheet, a thick plastic composite sheet, and a metal plate; or a flexible sheet, such as, a thin glass sheet, a thin plastic sheet, a thin plastic composite sheet, and metal foil. Examples of suitable materials for the substrate 170 include glass, which may be rigid or flexible; plastics such as polyethylene terephthalate, polybutylene phthalate, polyethylene naphthalate, polystyrene, polycarbonate, polyether sulfone, polyallylate, polyimide, polycycloolefin, norbornene resins, and fluoropolymers; metals such as stainless steel, aluminum, silver and gold; metal oxides such as titanium oxide and zinc oxide; and semiconductors such as silicon. In one particular embodiment, the substrate includes a polycarbonate.

As shown in FIGS. 1-15, the scintillator layer 140, the organic photodiode 130, and the TFT array 120 are enclosed inside an encapsulation cover 160 to protect them from the moisture and oxygen introduced from the atmosphere. In some embodiments, one or more additional seals 180 may be provided to provide effective sealing between the encapsulation cover 160 and the substrate 170.

In some embodiments of the invention, apart from being protected from the external moisture and oxygen, the organic photodiode 130 may be further protected from the oxygen and/or moisture that may be introduced (for example, from the scintillator layer 140) during the formation of the organic x-ray detector 100 or during operation of the organic x-ray detector 100.

At least one of an oxygen getter layer and a moisture getter layer may be further provided in the organic x-ray detector 100 to provide this protection. The oxygen getter layer and the moisture getter layers are disposed proximate to the organic photodiode 130. The term "disposed proximate" as used herein means that the oxygen and moisture getter layers are either disposed directly in contact with the organic photodiode 130; or at a distance such that the organic photodiode 130 is protected from exposure to oxygen and/or moisture because of the oxygen and moisture getter layers. Further, the oxygen and the moisture getter layers are disposed in the path of an x-ray radiation 20 incident on the layered structure 110 such that the x-ray radiation 20 passes through at least a portion of the oxygen and getter layers before reaching the organic photodiode 130.

The moisture getter layer may include any suitable material selected from the group consisting of alkali metals, alkaline earth metals, alkali metal oxides, alkaline earth metal oxides, aluminum oxide, zeolite, silica, and combinations thereof. Non limiting examples of suitable alkaline metals include calcium, barium, or combinations thereof. Not limiting examples of suitable oxides include calcium oxide, barium oxide, aluminum oxide, or combinations thereof.

The oxygen getter layer may include any suitable material selected from the group consisting of ether-containing materials, ascorbic acids, polyhydric alcohols, alkylene glycols, and combinations thereof. In certain embodiments, the oxygen getter layer includes an ether-containing material. Non-limiting examples of suitable ether-containing materials include polyethers, crown ethers, epoxy resins, or combinations thereof. In some embodiments, the ether-containing material may include a polymer that includes a polyether moiety. The polyether moiety may be present as a homopolymer, as a block in a block copolymer, or as a side chain on another polymer (i.e. as a comb polymer). There is no limitation on the polymer morphology, that is, the polymers may be linear, branched, crosslinked, networked, or cyclic. Further, any suitable molecular weight may be used such that a liquid or a solid material can be obtained. Also, as the oxidation mechanism is independent of endgroup chemistry, there is no limitation on endgroup chemistry, and the nature of the two endgroups can be different. For example, one or both endgroups may be hydrogen, methyl, higher alkyl, vinyl, epoxy, thiol, glycidyl, tosylate, or an ester. The ester could be an acrylate or a methacrylate, thereby allowing polymerization of the polyether moiety either by itself or as a mixture with other monomers.

In some embodiments, the ether-containing material includes a poly(alkylene glycol), such as, for example, poly(ethylene glycol), poly(propylene glycol), poly(butylene glycol), or combinations thereof.

In some embodiments, the ether-containing material includes bifunctional ethylene glycol or poly(ethylene glycol). Non-limiting examples of suitable ether-containing materials include:

ethylene glycol diacrylate having a chemical structure (I):

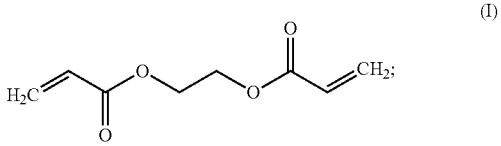

poly(ethylene glycol)diacrylate having a chemical structure (II):

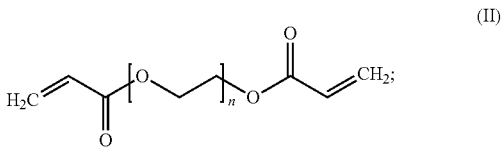

poly(ethylene glycol)diglycidyl ether having a chemical structure (III):

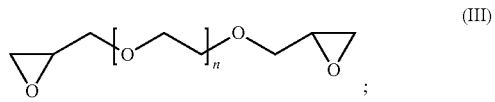

poly(ethylene glycol)dithiol having a chemical structure (IV):

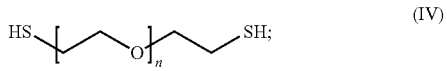

poly(ethylene glycol)divinyl ether having a chemical structure (V):

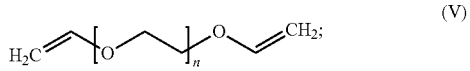

or
poly(ethylene glycol)-di-tosylate having a chemical structure (VI):

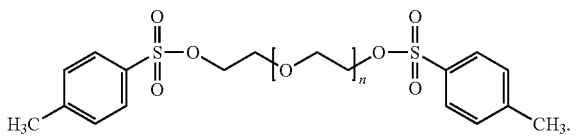

Crosslinking promoters such as photoinitiators, thermal-initiators, radical initiators, photo-acid generators, and photo-base generators may be further added to the bifunctional ether-containing material to initiate cross-linking reactions and/or enhance the degree of cross-linking. Non-limiting examples of suitable promoters include ethylbenzoyn ether, isopropylbenzoyn ether, α-methylbenzoyn ethyl ether, benzoyn phenyl ether, α-acyloxime ester, α,α-diethoxy acetophenone, 1,1-dichloroacetophenone, 2-hydroxy-2-methyl-1-phenylpropane-1-one [Darocure 1173 of Ciba Specialty Chemicals], 1-hydroxycyclohexyl phenyl ketone [Irgacure 184, Darocure 1116, Irgacure 907 of Ciba Specialty Chemicals], bis(2,4,6-trimethylbenzoyl)-phenylphosphineoxide (Irgacure 819 of Ciba Specialty Chemicals], anthraquinone, 2-ethyl anthraquinone, 2-chloro anthraquinone, thioxanthone, isopropyl thioxanthone, chlorothioxanthone, benzophenone, p-chlorobenzophenone, benzyl benzoate, benzoyl benzoate and Michler's ketone. Non-limiting examples of suitable thermal initiators include azoisobutyronitrile-based and peroxide-based initiators.

In some embodiments, the ether-containing material may be used in essentially pure form relying on adventitious radicals or x-rays to create the free radicals that can react with oxygen. Alternatively, a catalyst may be further used to generate radicals. Effective catalysts generally have a plurality of oxidation states readily available and include transition metals such as iron, cobalt, and copper.

In some embodiments, the oxygen-getter layer may further include a transition metal catalyst, for example, a cobalt salt, an iron salt, a copper salt, or combinations thereof. The transition metals may be introduced as salts of carboxylic acids to give good compatibility with the polyether. Non-limiting examples of suitable catalysts include copper acetate, copper octanoate, cobalt acetate, cobalt octanoate, or combinations thereof.

As mentioned previously, a layer includes material disposed on at least a portion of an underlying surface in a continuous or discontinuous manner. Further, the term "layer" does not necessarily mean a uniform thickness of the disposed material, and the disposed material may have a uniform or a variable thickness. In some embodiments, one or both of the oxygen getter layer and the moisture getter layer may have any suitable shape, non-limiting examples of which include a continuous layer, a strip, a patch, or combinations thereof. Further, one or both of the oxygen getter layer and the moisture getter may be primarily comprised of the suitable getter material; or alternately may further include a binder and the getter material may be dispersed in the binder.

Figure 2:
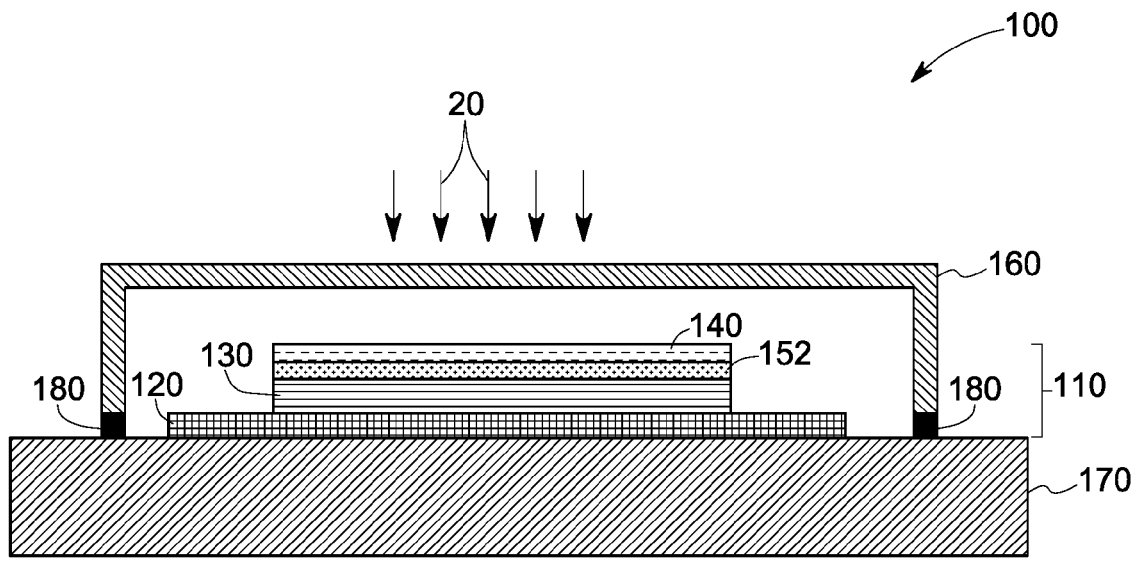
FIG. 2 is a schematic of an organic x-ray detector, according to one embodiment of the invention.
Figure 3:
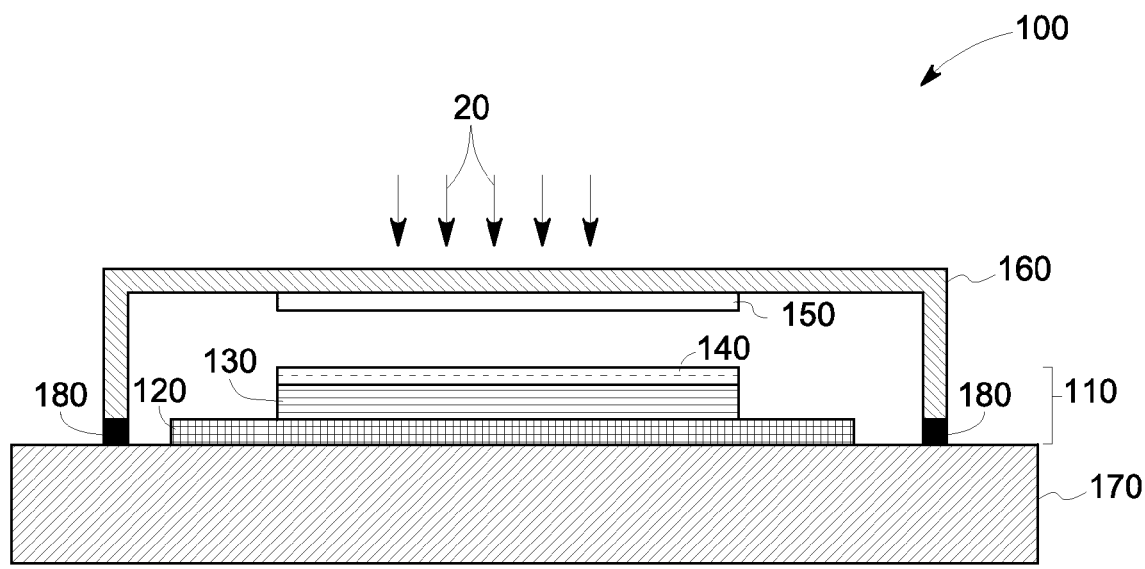
FIG. 3 is a schematic of an organic x-ray detector, according to one embodiment of the invention.
Figure 4:
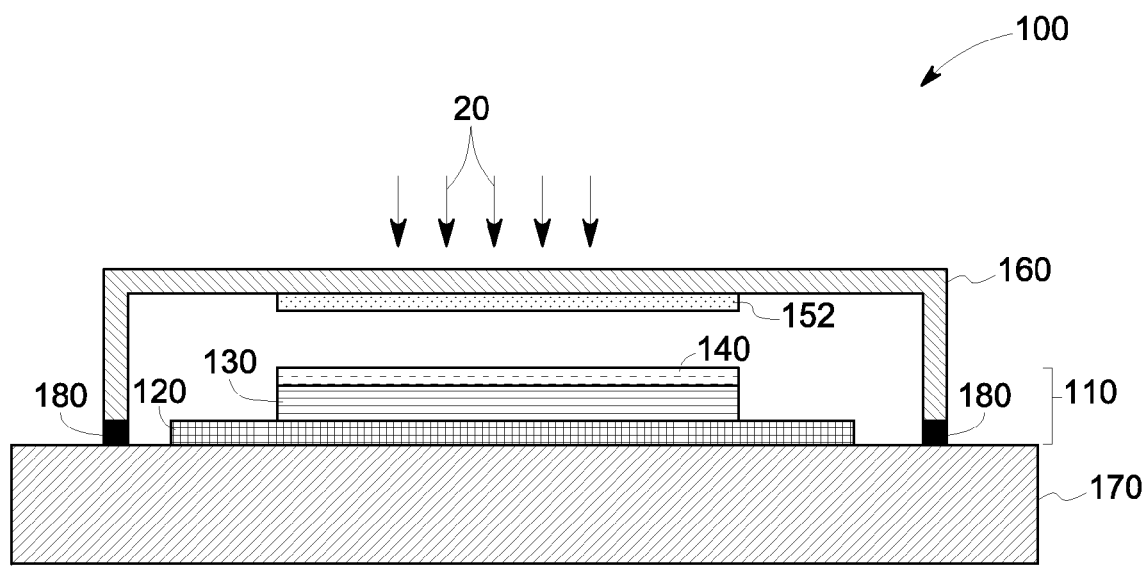
FIG. 4 is a schematic of an organic x-ray detector, according to one embodiment of the invention.

FIGS. 1-4 illustrate embodiments including an oxygen getter layer 150 or a moisture getter layer 152. In FIGS. 1 and 2, the oxygen getter layer 150 or the moisture getter layer 152 is disposed in the layered structure 110. In alternate embodiments, the oxygen getter layer 150 or the moisture getter layer 152 is disposed in contact with at least a portion of the encapsulation cover 160, as shown in FIGS. 3 and 4.

In some embodiments as shown in FIGS. 5-15, the organic x-ray detector 100 includes both the oxygen getter layer 150 and the moisture getter layer 152. The oxygen-getter layer 150 and the moisture getter layer 152 may have any suitable configuration in the organic x-ray detector 100 provided that the getter layers are disposed in the path of the x-ray radiation 20. In some embodiments, the moisture getter layer 152 and the oxygen getter layer 150 may be disposed as two separate layers 150, 152, as shown in FIGS. 5, 7, 9, 11, 12 and 15. In some other embodiments, the moisture getter layer 152 and the oxygen getter layer 150 are disposed as a single layer 151, as shown in FIGS. 6, 8, 10, 13 and 14.

Further, at least one of the oxygen getter layer 150 and the moisture getter layer 152 may be a component of the layered structure 110, as shown in FIGS. 5-8. Alternately, at least one of the oxygen getter layer 150 and the moisture getter layer 152 may be disposed such that at least a portion of the oxygen getter layer 150 or the moisture getter layer 152 is in contact with the encapsulation cover 160, as show in FIGS. 9-15.

In some embodiments, the layered structure 110 includes at least one of the moisture getter layer 152 and the oxygen getter layer 150. In some embodiments, the layered structure 110 includes both the moisture getter layer 152 and the oxygen getter layer 150. In some instances wherein the layered structure 110 includes the getter layer, at least one of the moisture getter layer 152 and the oxygen getter layer 150 may be interposed between the organic photodiode 130 and the scintillator layer 140. In other instances, at least one of the moisture getter layer 152 and the oxygen getter layer 150 may be disposed on the scintillator layer 140. the moisture getter layer and the oxygen getter layer may be disposed on the scintillator layer.

Figure 5:
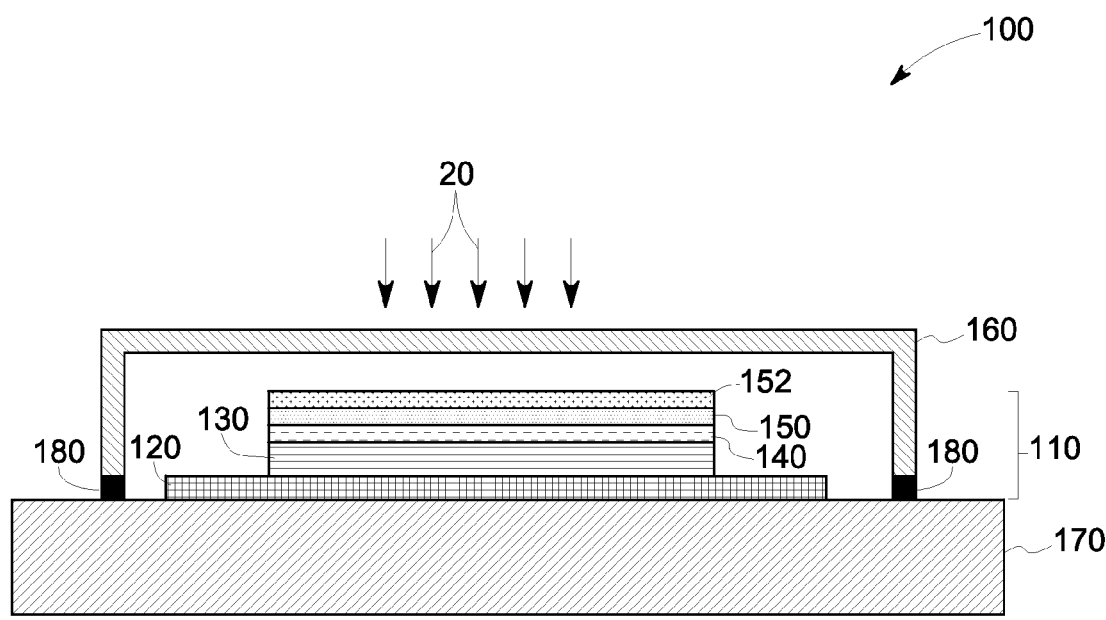
FIG. 5 is a schematic of an organic x-ray detector, according to one embodiment of the invention.
Figure 6:
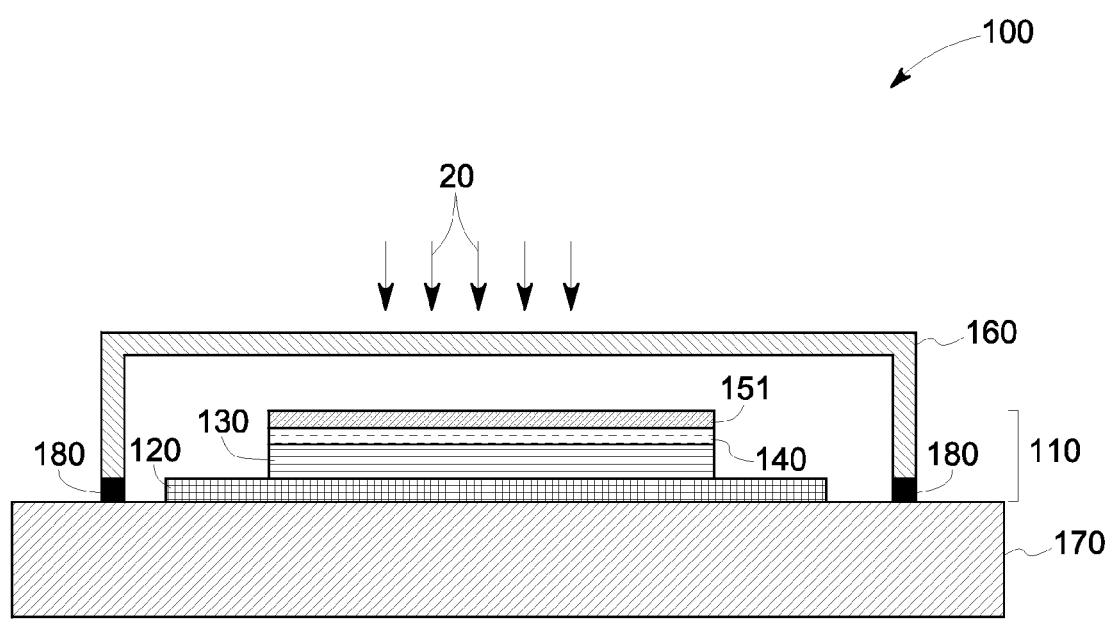
FIG. 6 is a schematic of an organic x-ray detector, according to one embodiment of the invention.

FIG. 5 illustrates an embodiment of an organic x-ray detector 100 wherein the oxygen getter layer 150 is disposed on top of the scintillator layer 140 and the moisture getter layer 152 is disposed on the oxygen getter layer 150. In other embodiments (not shown in Figures), the moisture getter layer 152 may be disposed on top of the scintillator layer 140, and the oxygen getter layer 150 may be disposed on the moisture getter layer 152. FIG. 6 illustrates an alternative embodiment of an organic x-ray detector 100 wherein the oxygen getter layer 150 and the moisture getter layer 152 are disposed as a single layer 151 on the scintillator layer 140.

Figure 7:
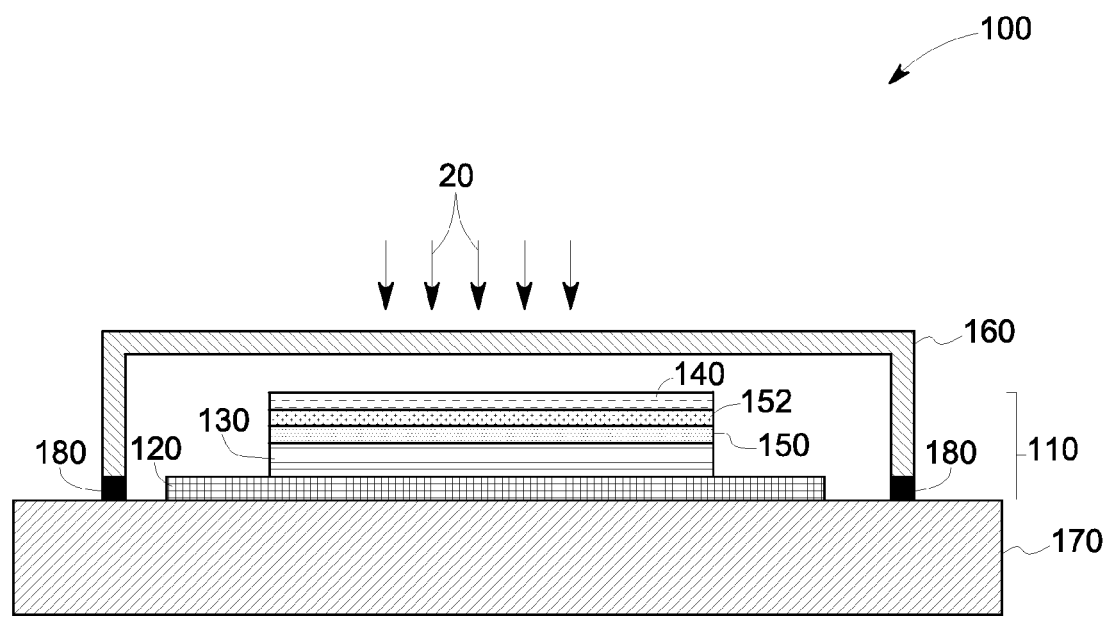
FIG. 7 is a schematic of an organic x-ray detector, according to one embodiment of the invention.
Figure 8:
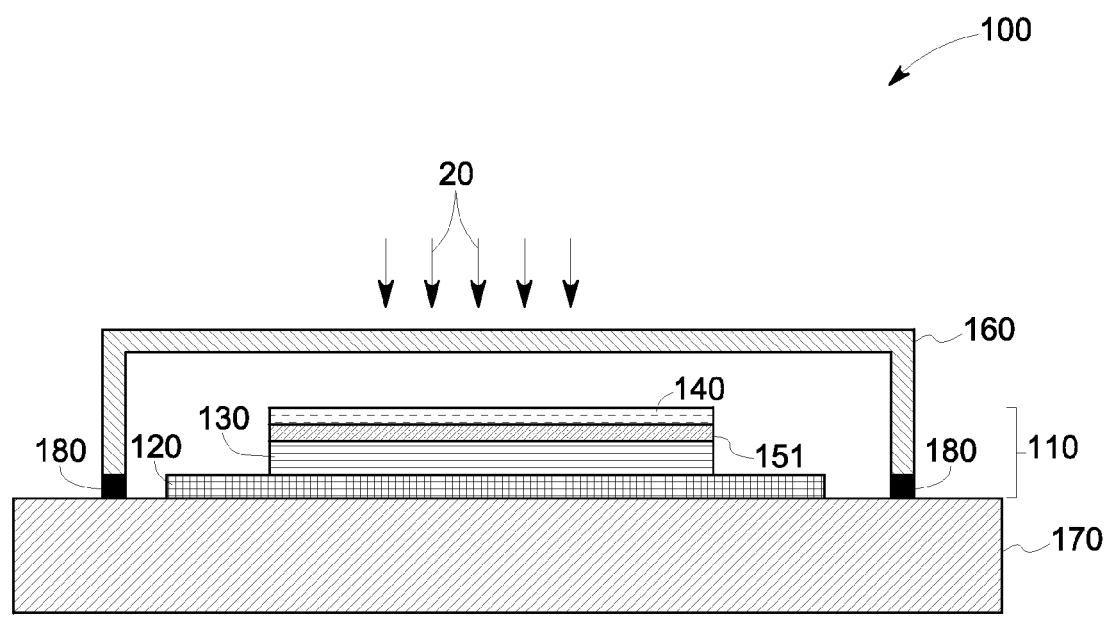
FIG. 8 is a schematic of an organic x-ray detector, according to one embodiment of the invention.

FIG. 7 illustrates an embodiment of an organic x-ray detector 100 wherein the oxygen and moisture getter layers 150, 152 are interposed between the scintillator layer 140 and the organic photodiode 130. In the embodiment illustrated in FIG. 7, the oxygen getter layer 150 is disposed on the organic photodiode 130, and the moisture getter layer 152 is disposed on the oxygen getter layer 150. In other embodiments (not shown in Figures), the moisture getter layer 152 may be disposed on the organic photodiode 130, and the oxygen getter layer 150 may be disposed on the moisture getter layer 152. FIG. 8 illustrates an alternative embodiment of an organic x-ray detector 100 wherein the oxygen getter layer 150 and the moisture getter layer 152 are disposed as a single layer 151 between the organic photodiode 130 and the scintillator layer 140.

In some other embodiments, at least one of the moisture getter layer 152 and the oxygen getter layer 150 is disposed in contact with at least a portion of the encapsulation cover 160. In some such instances, both the moisture getter layer 152 and the oxygen getter layer 150 are disposed in contact with at least a portion of the encapsulation cover 160. Further, in some such instances, at least one of the moisture getter layer 152 and the oxygen getter layer 150 substantially encapsulates the layered structure 110.

Figure 9:
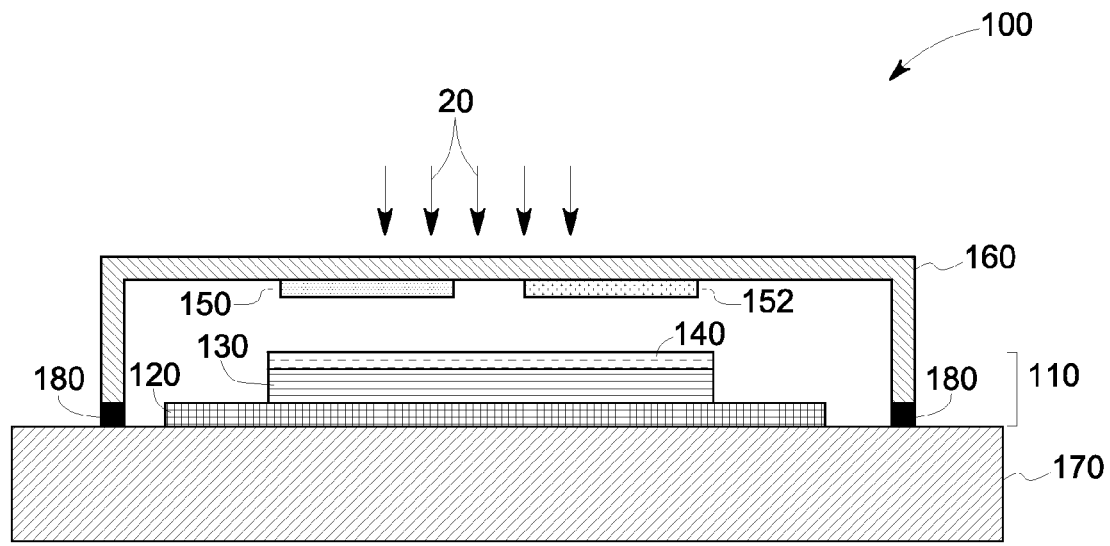
FIG. 9 is a schematic of an organic x-ray detector, according to one embodiment of the invention.
Figure 10:
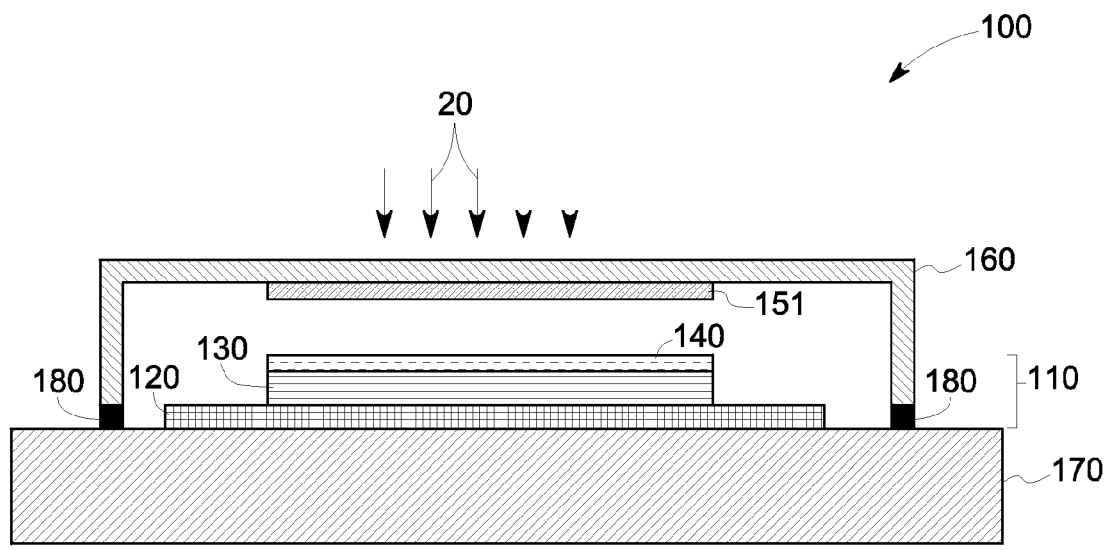
FIG. 10 is a schematic of an organic x-ray detector, according to one embodiment of the invention.
Figure 11:
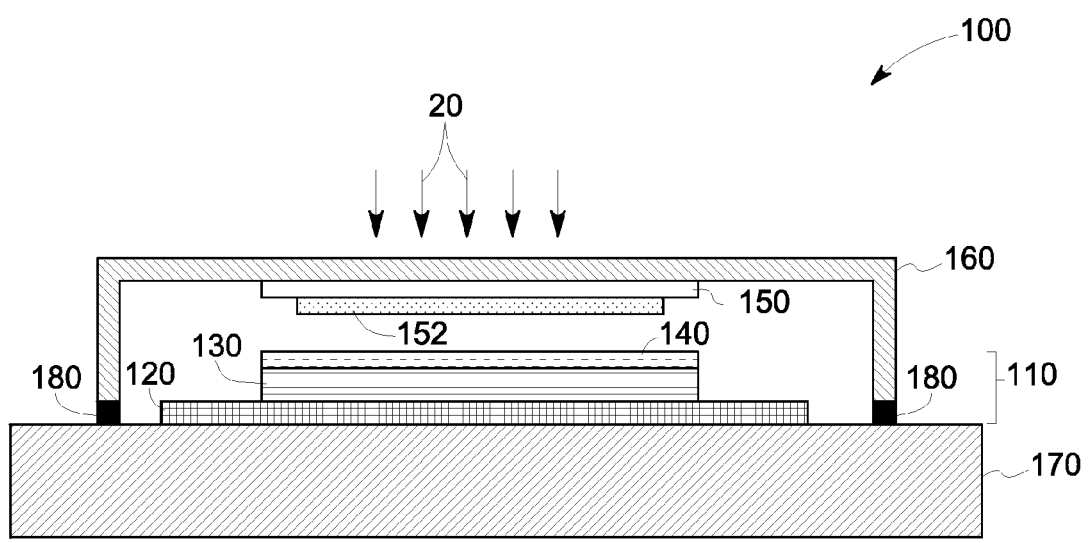
FIG. 11 is a schematic of an organic x-ray detector, according to one embodiment of the invention.

FIG. 9 illustrates an embodiment of an organic x-ray detector 100 wherein both the oxygen getter layer 150 and the moisture getter layer 152 are disposed in contact with at least a portion of the encapsulation cover 160. FIG. 10 illustrates an alternate embodiment of an organic x-ray detector 100, wherein the oxygen getter layer 150 and the moisture getter layer 152 are disposed as a single layer 151 in contact with at least a portion of the encapsulation cover 160. FIG. 11 illustrates an embodiment of the of an organic x-ray detector 100 wherein the oxygen getter layer 150 is disposed in contact with at least a portion of the encapsulation cover 160 and the moisture getter layer 152 is disposed in contact with the oxygen getter layer 150.

Figure 12:
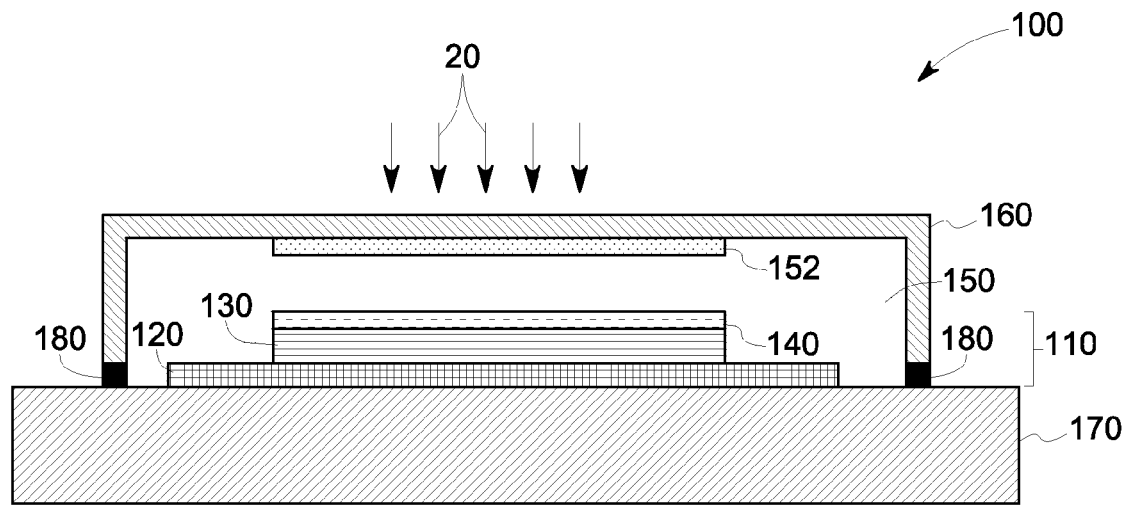
FIG. 12 is a schematic of an organic x-ray detector, according to one embodiment of the invention.
Figure 13:
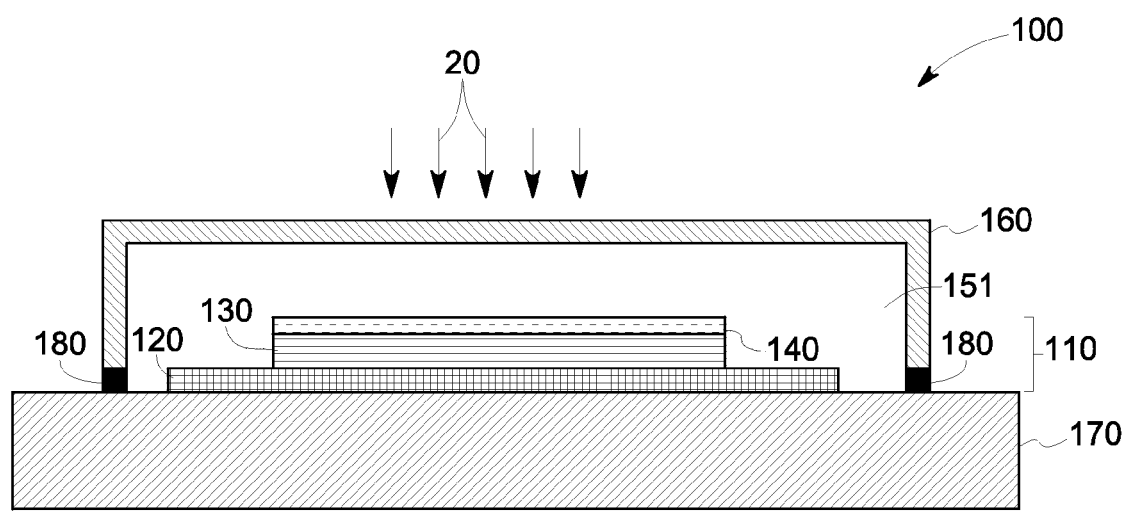
FIG. 13 is a schematic of an organic x-ray detector, according to one embodiment of the invention.
Figure 14:
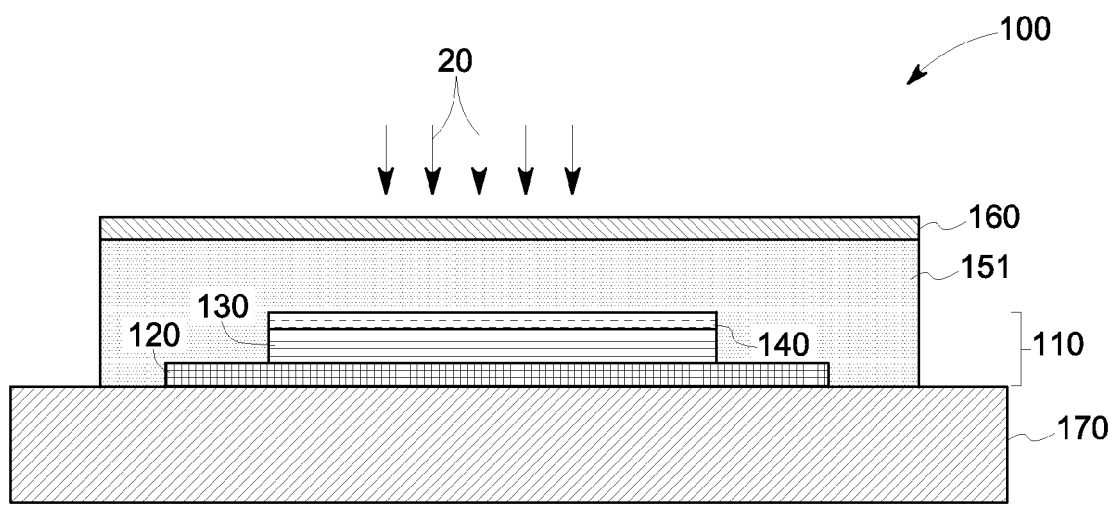
FIG. 14 is a schematic of an organic x-ray detector, according to one embodiment of the invention.

FIG. 12 illustrates an embodiment of an organic x-ray detector 100 wherein the oxygen getter layer 150 substantially encapsulates the layered structure 110, and the moisture getter layer 152 is disposed in contact with at least a portion of the encapsulation cover 160. FIG. 13 illustrates an alternate embodiment of an organic x-ray detector 100, wherein the oxygen getter layer 150 and the moisture getter layer 152 are disposed as a single layer 151 substantially encapsulating the layered structure 110. In FIG. 13, the encapsulation cover 160 and the seals 180 may further provide a sealing arrangement from the outside environment. Alternately, as shown in FIG. 14, the single layer 151 itself may provide sealing from the outside environment.

Figure 15:
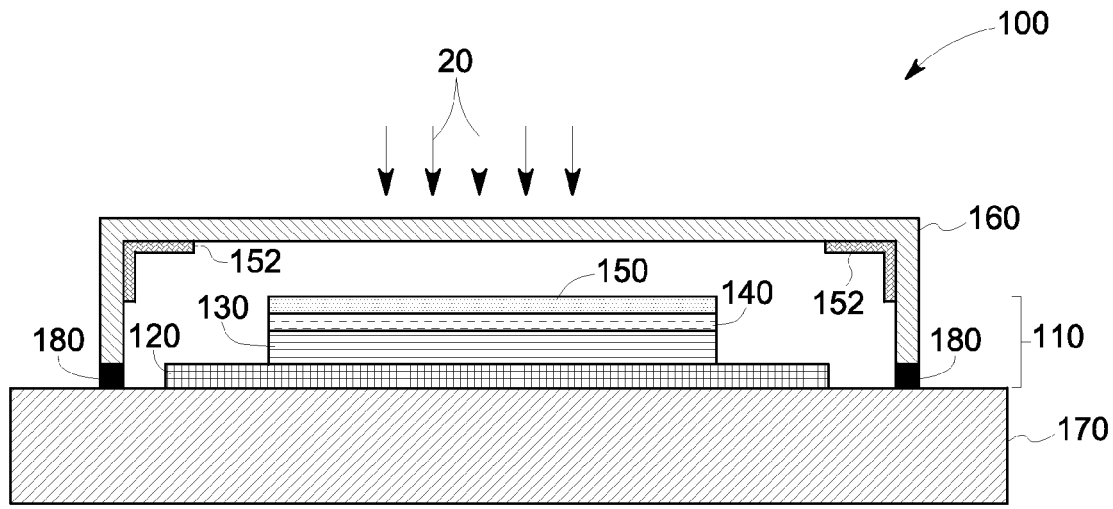
FIG. 15 is a schematic of an organic x-ray detector, according to one embodiment of the invention.

FIG. 15 illustrates another embodiment of an organic x-ray detector 100 including an oxygen getter layer 150 and a moisture getter layer 152. As shown in FIG. 15, the layered structure 110 includes the oxygen getter layer 150 and the moisture getter layer 152 is disposed in contact with at least a portion of the encapsulation cover 160.

Without being bound by any theory it is believed that the incorporation of the oxygen getter layer 150 and the moisture getter layer 152 may improve device reliability by trapping oxygen and moisture that otherwise can degrade performance of the organic x-ray detector 100.

Figure 17:
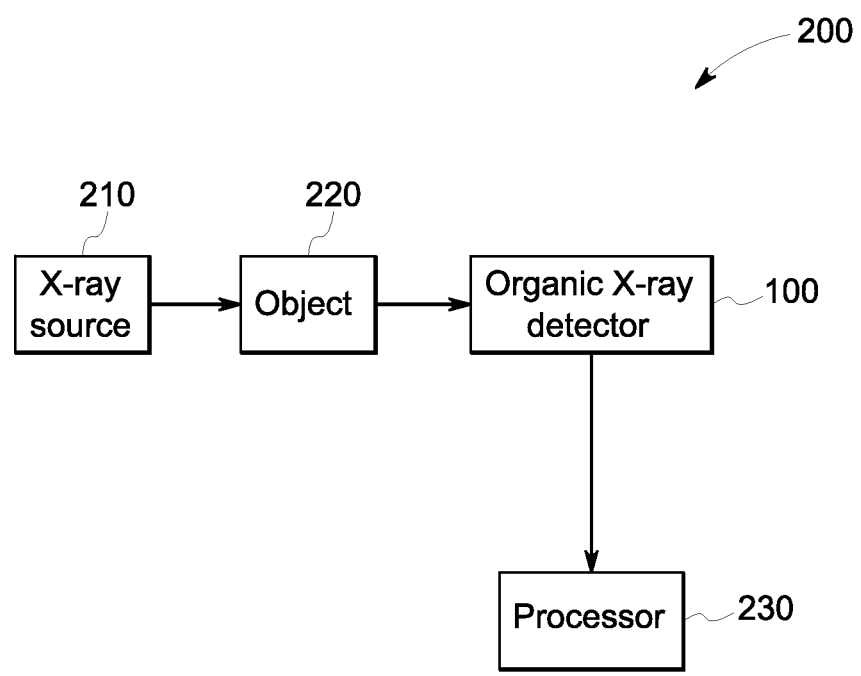
FIG. 17 is schematic of an x-ray system, according to one embodiment of the invention.
Figure 18A:
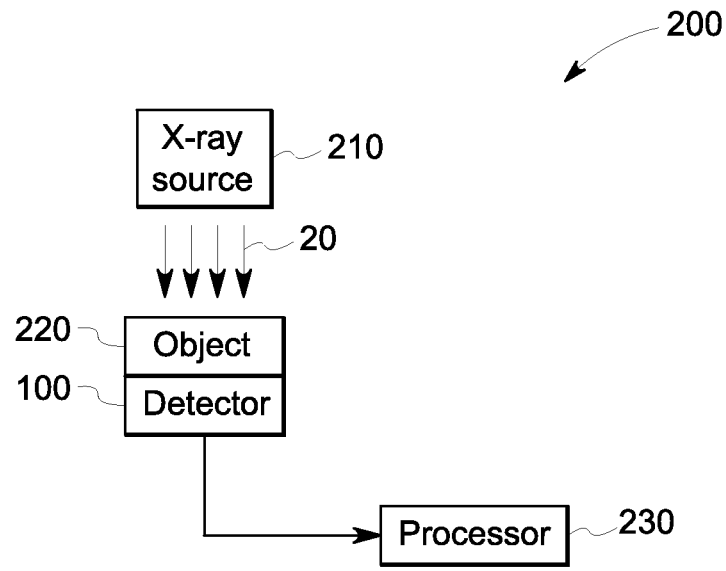
FIG. 18A is schematic of an x-ray system, according to one embodiment of the invention.
Figure 18B:
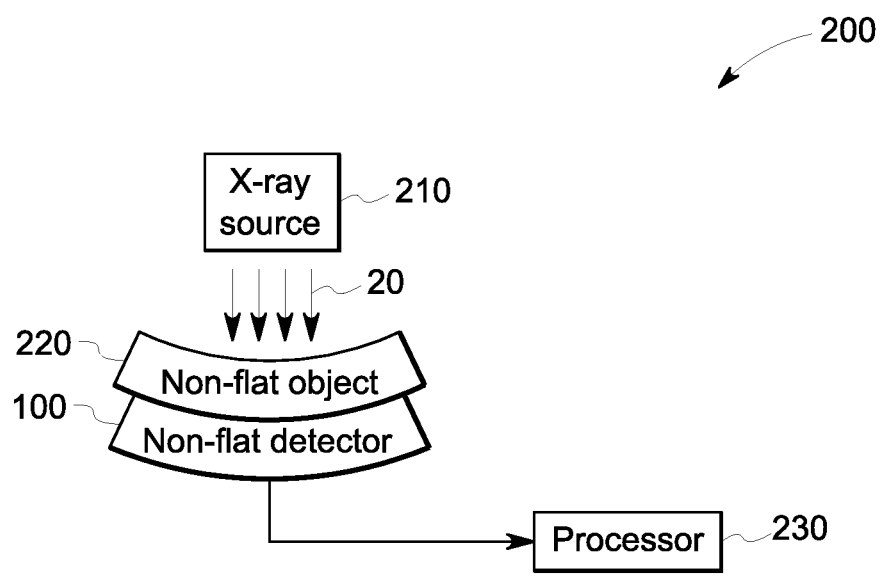
FIG. 18B is schematic of an x-ray system, according to one embodiment of the invention.

In some embodiments, an x-ray system 200 is also presented. As shown in FIG. 17, the x-ray system 200 includes an x-ray source 210 configured to irradiate an object 220 with x-ray radiation see figures, an organic x-ray detector 100 as described earlier, and a processor 230 operable to process data from the organic x-ray detector 100. FIGS. 18A and 18B further show embodiments of the x-ray system 200 suitable for substantially flat objects or objects with a curved shape. As shown in FIGS. 18A and 18B, the organic x-ray detector 100 may have a shape suitable for the object 220. In FIGS. 18A and 18B, the processor 230 may be communicatively coupled to the organic x-ray detector 100 using a wired or a wireless connection.

An organic x-ray detector 100 according to embodiments of the present invention may be used in imaging systems, for example, in conformal imaging, with the organic x-ray detector 100 in intimate contact with the imaging surface. For parts with internal structure, the organic x-ray detector 100 may be rolled or shaped to contact the part being imaged. Applications for the organic x-ray detectors according to embodiments of the present invention include security imaging; medical imaging; and industrial and military imaging for pipeline, fuselage, airframe and other tight access areas.

EXAMPLES

Comparative Example 1

X-Ray Detector Imager without Oxygen or Moisture Getter Layers

Glass based thin-film-transistor (TFT) array pre-coated with ITO was used as the substrate. A hole-transport layer was deposited onto ultraviolet-ozone treated TFT array substrates via spin-coating and then baked on a hotplate. An absorber layer consisting of a fullerene based acceptor and a donor material was then spin-coated on top of the hole-transport layer inside of a $N_2$ purged glovebox. The imager fabrication was completed with sputtering of the ITO cathode. Next the DRZ-Plus scintillator (Mitsubishi Chemical) made of gadolinium sulfoxylate doped with terbium ($Gd_2O_2S$:Tb) was laminated to the imager using a pressure sensitive adhesive (PSA) film from 3M under the product name of 8191L. The imager was encapsulated using a cover glass and an edge sealant.

Example 1

X-Ray Detector Imager with a Moisture Getter Layer

The imager prepared in Example 1 was sealed in the same way as Comparative Example 1 except with the incorporation of a moisture getter, DryFlex, which was purchased from SAES Getters Group.

Example 2

X-Ray Detector Imager with an Oxygen Getter Layer

The imager prepared in Example 2 was sealed in the same way as Comparative Example 1 except with the incorporation of an oxygen getter, poly(ethylene glycol) 600 diacrylate, which was purchased from Sartomer under the product name of SR610 and mixed with the cobalt(II) acetate tetrahydrate catalyst and 1% by weight Irgacure 819 photoinitiator. The SR610-based oxygen getter layer was cured under UV irradiation.

Example 3

X-Ray Detector Imager with Both the Oxygen and Moisture Getter Layers

The imager prepared in Example 3 was sealed in the same way as Comparative Example 1 except with the incorporation of both the oxygen getter layer of Example 2 and the moisture getter of Example 1. The layers had a configuration similar to that of FIG. 11.

Comparative Example 2

X-Ray Detector Imager without Oxygen or Moisture Getter Layers

The imager prepared in Comparative Example 2 was prepared in the same way as Comparative Example 1 except that it further included an organic smoothing layer; and an ITO barrier coating between the ITO cathode and the scintillator layer. The organic smoothing layer consisting of a UV cross-linkable acrylate was applied on top of the ITO via screen printing and UV cured. The ITO moisture barrier layer was then sputtered on top of the smoothing layer.

Example 4

X-Ray Detector Imager with a Moisture Getter Layer

The imager prepared in Example 4 was prepared in the same way as Comparative Example 2 except with the incorporation of a moisture getter, DryFlex, which was purchased from SAES Getters Group.

Example 5

X-Ray Detector Imager with Both the Oxygen the Moisture Getter Layers

The imager prepared in Example 5 was sealed in the same way as Comparative Example 2 except with the incorporation of both the oxygen getter layer of Example 2 and the moisture getter of Example 1. The layers had a configuration similar to that of FIG. 11.

Reliability of the imagers was then tested at 85° C. and 85% relative humidity. Performance was characterized using x-ray imager functional tester. The increase in the number of defects is summarized in Table 1 and Table 2. As one can see, incorporating getter materials s reduced the change in defect counts and improved imager stability. Further the increase in number of defects reduced significantly when both the getter layers were used.

TABLE 1

Increase in number of defects for imagers with and without getter materials

| Example | Moisture Getter | Oxygen Getter | Hours at 85° C./85% | Increase in number of defects |
|---|---|---|---|---|
| Comparative Example 1 | No | No | 336 | 57 |
| Example 1 | Yes | No | 336 | 39 |
| Example 2 | No | Yes | 336 | 46 |
| Example 3 | Yes | Yes | 336 | 5 |

TABLE 2

Increase in number of defects for imagers with and without getter materials

| Example | Moisture Getter | Oxygen Getter | Hours at 85° C./85% | Increase in number of defects |
|---|---|---|---|---|
| Comparative Example 2 | No | No | 576 | 93 |
| Example 4 | Yes | No | 505 | 0 |
| Example 5 | Yes | Yes | 562 | 0 |

The foregoing examples are merely illustrative, serving to exemplify only some of the features of the invention. The appended claims are intended to claim the invention as broadly as it has been conceived and the examples herein presented are illustrative of selected embodiments from a manifold of all possible embodiments. Accordingly, it is the Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied; those ranges are inclusive of all sub-ranges there between. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims.

The invention claimed is:

1. An x-ray detector, comprising:
    a layered structure comprising:
        a substrate,
        a thin-film transistor (TFT) array disposed on the substrate,
        an organic photodiode disposed on the TFT array, and
        a scintillator layer disposed on the organic photodiode;
    an encapsulation cover at least partially encapsulating the layered structure; and
    at least one of a moisture getter layer and an oxygen getter layer disposed proximate to the organic photodiode, and in the path of an x-ray radiation incident on the layered structure.

2. The x-ray detector of claim 1, wherein the moisture getter layer and the oxygen getter layer are disposed as two or more separate layers.

3. The x-ray detector of claim 1, wherein the layered structure comprises at least one of the moisture getter layer and the oxygen getter layer.

4. The x-ray detector of claim 3, wherein the layered structure comprises both the moisture getter layer and the oxygen getter layer.

5. The x-ray detector of claim 3, wherein at least one of the moisture getter layer and the oxygen getter layer is interposed between the organic photodiode and the scintillator layer.

6. The x-ray detector of claim 3, wherein at least one of the moisture getter layer and the oxygen getter layer is disposed on the scintillator layer.

7. The x-ray detector of claim 1, wherein at least one of the moisture getter layer and the oxygen getter layer substantially encapsulates the layered structure.

8. The x-ray detector of claim 1, wherein at least one of the moisture getter layer and the oxygen getter layer is disposed in contact with at least a portion of the encapsulation cover.

9. The x-ray detector of claim 8, wherein the oxygen getter layer is disposed in contact with at least a portion of the encapsulation cover, and the moisture getter layer is disposed in contact with the oxygen getter layer.

10. The x-ray detector of claim 1, wherein the layered structure comprises the oxygen getter layer and the moisture getter layer is disposed in contact with at least a portion of the encapsulation cover.

11. The x-ray detector of claim 1, wherein the moisture getter layer comprises alkali metals, alkaline metals, alkali metal oxides, alkaline metal oxides, aluminum oxide, zeolite, silica, or combinations thereof.

12. The x-ray detector of claim 1, wherein the oxygen getter layer comprises polyethers, crown ethers, ascorbic acid, polyhydric alcohols, alkylene glycols, or combinations thereof.

13. The x-ray detector of claim 1, wherein the substrate comprises a material selected from the group consisting of glass, metal foil, plastic, and combinations thereof.

14. The x-ray detector of claim 1, wherein the TFT array comprises a silicon TFT array, an oxide TFT array, an organic TFT, or combinations thereof.

15. An x-ray detector, comprising:
    a layered structure comprising:
        a substrate,
        a thin-film transistor (TFT) array disposed on the substrate,
        an organic photodiode disposed on the TFT array, and
        a scintillator layer disposed on the organic photodiode;
    an encapsulation cover at least partially encapsulating the layered structure;
    an oxygen getter layer disposed between the organic photodiode and the scintillator layer in the layered structure; and
    a moisture getter layer disposed in contact with at least a portion of the encapsulation cover.

16. An x-ray system, comprising:
    an x-ray source;
    an x-ray detector comprising:
        a layered structure comprising:
            a substrate,
            a thin-film transistor (TFT) array disposed on the substrate, an organic photodiode disposed on the TFT array, and a scintillator layer disposed on the organic photodiode;

an encapsulation cover at least partially encapsulating the layered structure; and at least one of a moisture getter layer and an oxygen getter layer disposed proximate to the organic photodiode, and in the path of an x-ray radiation incident on the layered structure; and a processor operable to process data from the X-ray detector.

17. The x-ray system of claim 16, wherein the layered structure comprises at least one of the moisture getter layer and the oxygen getter layer.

18. The x-ray system of claim 16, wherein at least one of the moisture getter layer and the oxygen getter layer is disposed in contact with at least a portion of the encapsulation cover.

19. The x-ray system of claim 16, wherein the moisture getter layer and the oxygen getter layer are disposed as two or more separate layers.

20. The x-ray system of claim 16, wherein the layered structure comprises the oxygen getter layer and the moisture getter layer is disposed in contact with at least a portion of the encapsulation cover.

* * * * *